(12) United States Patent
Focht et al.

(10) Patent No.: US 7,511,003 B2
(45) Date of Patent: *Mar. 31, 2009

(54) STRIPED LIQUID PERSONAL CLEANSING COMPOSITIONS CONTAINING A CLEANSING PHASE AND A SEPARATE BENEFIT PHASE WITH IMPROVED STABILITY

(75) Inventors: Heather Lynn Focht, Hamilton, OH (US); Christopher Dean Putman, West Chester, OH (US); Cheyne Pohlman Thomas, Independence, KY (US); Karl Shiqing Wei, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/699,469

(22) Filed: Oct. 31, 2003

(65) Prior Publication Data

US 2004/0092415 A1 May 13, 2004

Related U.S. Application Data

(60) Provisional application No. 60/423,537, filed on Nov. 4, 2002.

(51) Int. Cl.
*A61K 7/00* (2006.01)
(52) U.S. Cl. .................. 510/130; 510/427; 510/475; 510/510; 206/77.1
(58) Field of Classification Search ............ 510/130, 510/156, 153, 440, 504, 499
See application file for complete search history.

(56) References Cited

U.S. PATENT DOCUMENTS

| | | |
|---|---|---|
| 3,479,429 A | 11/1969 | Morshauser et al. |
| 3,533,955 A | 10/1970 | Pader et al. |
| 3,937,811 A | 2/1976 | Papantoniou et al. |
| 3,980,767 A | 9/1976 | Chown et al. |
| 4,159,028 A | 6/1979 | Barker et al. |
| 4,263,363 A | 4/1981 | Buck et al. |
| 4,335,103 A | 6/1982 | Baker et al. |
| 4,425,322 A | 1/1984 | Harvey et al. |
| 4,518,578 A | 5/1985 | Hayes et al. |
| 4,966,205 A | 10/1990 | Tanaka |
| 4,980,155 A | 12/1990 | Shah et al. |
| 5,059,414 A | 10/1991 | Dallal et al. |
| 5,304,334 A | 4/1994 | Lahanas et al. |
| 5,393,450 A | 2/1995 | Shana'a et al. |
| 5,455,035 A | 10/1995 | Guerrero et al. |
| 5,556,628 A | 9/1996 | Derian et al. |
| 5,612,307 A | 3/1997 | Chambers et al. |
| 5,635,171 A | 6/1997 | Nadaud et al. |
| 5,851,978 A | 12/1998 | Shana'a |
| 5,914,117 A * | 6/1999 | Lavaud .................. 424/401 |
| 5,929,019 A | 7/1999 | Puvvada et al. |
| 5,947,335 A | 9/1999 | Milio et al. |
| 5,952,286 A | 9/1999 | Puvvada et al. |
| 5,965,500 A | 10/1999 | Puvvada |
| 5,965,501 A * | 10/1999 | Rattinger et al. ............ 510/146 |
| 6,174,845 B1 * | 1/2001 | Rattinger et al. ............ 510/146 |
| 6,176,391 B1 | 1/2001 | Rehkemper et al. |
| 6,176,395 B1 | 1/2001 | Abbott et al. |
| 6,213,166 B1 | 4/2001 | Thibiant et al. |
| 6,245,344 B1 | 6/2001 | Thibiant et al. |
| 6,268,322 B1 | 7/2001 | St. Lewis et al. |
| 6,306,806 B1 * | 10/2001 | St. Lewis et al. ............ 510/159 |
| 6,383,999 B1 | 5/2002 | Coyle et al. |
| 6,429,177 B1 * | 8/2002 | Williams et al. ............ 510/130 |
| 6,506,391 B1 | 1/2003 | Biatry |
| 6,521,216 B1 | 2/2003 | Glandorf et al. |
| 6,534,456 B2 * | 3/2003 | Hayward et al. ............ 510/130 |
| 6,534,457 B2 * | 3/2003 | Mitra ........................ 510/130 |
| 6,589,509 B2 | 7/2003 | Keller et al. |
| 2001/0036467 A1 | 11/2001 | Thibiant et al. |
| 2002/0004468 A1 | 1/2002 | Hodge et al. |
| 2002/0010110 A1 | 1/2002 | Hayward et al. |
| 2003/0180246 A1 | 9/2003 | Frantz et al. |
| 2004/0048757 A1 | 3/2004 | Zhang et al. |
| 2004/0048758 A1 | 3/2004 | Zhang et al. |
| 2004/0092415 A1 * | 5/2004 | Focht et al. .................. 510/130 |
| 2004/0223993 A1 | 11/2004 | Clapp et al. |
| 2004/0242706 A1 | 12/2004 | Wiersema et al. |
| 2004/0248749 A1 | 12/2004 | Mitra et al. |
| 2005/0020468 A1 | 1/2005 | Frantz et al. |
| 2005/0249758 A1 | 11/2005 | Di Puccio Pagano |

FOREIGN PATENT DOCUMENTS

CA 2246316 6/1998

(Continued)

OTHER PUBLICATIONS

XP 002332778 "Dove All Day Moisturizing Body Wash" Online URL: http://www.ewg.org/reprots/skindeep/productinfo. php?prod_id=901910.
XP002332779 "Olay Daily Renewal Moisturizing Body Wash" Online URL: http://householdprdoucts.nlm.nih.gov/cgi-bin/household.brands?tbl=brands&id=16003084.
U.S. Appl. No. 10/050,494, filed Jan. 16, 2002, Wei et al.
U.S. Appl. No. 10/358,803, filed Feb. 5, 2003, Putnam et al.
U.S. Appl. No. 10/655,670, filed Sep. 18, 2003, Focht et al.

*Primary Examiner*—Necholus Ogden, Jr.
(74) *Attorney, Agent, or Firm*—S. Robert Chuey; Bridget Murray; Cynthia L. Clay

(57) ABSTRACT

Personal cleansing compositions comprise (A) a cleansing phase containing a surfactant and water; and (B) a separate benefit phase containing a hydrophobic material; wherein the cleansing and benefit phases are packaged together and are in physical contact. The two phases are packaged in physical contact and remain separate and stable at ambient conditions for at least 180 days. These compositions and corresponding methods provide improved cosmetics, skin feel, and/or skin benefit efficacy.

12 Claims, No Drawings

FOREIGN PATENT DOCUMENTS

| | | |
|---|---|---|
| DE | 19650952 A | 6/1998 |
| DE | 198 54 086 A | 5/2000 |
| EP | 0 078138 A2 | 5/1983 |
| EP | 0 331617 B | 4/1992 |
| EP | 1 005849 B1 | 9/2001 |
| EP | 0 907345 B1 | 5/2003 |
| GB | 1277324 A | 6/1972 |
| JP | 2000229817 A | 8/2000 |
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |
| WO | WO 98/33477 | 8/1998 |
| WO | WO 99/38489 A1 | 8/1999 |
| WO | WO 99/38491 A1 | 8/1999 |
| WO | WO 01/01931 A2 | 1/2001 |
| WO | WO 01/70926 A1 | 9/2001 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 A1 | 6/2004 |

* cited by examiner

STRIPED LIQUID PERSONAL CLEANSING COMPOSITIONS CONTAINING A CLEANSING PHASE AND A SEPARATE BENEFIT PHASE WITH IMPROVED STABILITY

CROSS REFERENCE TO RELATED APPLICATION

This application claims the benefit of U.S. Provisional Application No. 60/423,537, filed Nov. 4, 2002.

FIELD OF THE INVENTION

The present invention relates to striped liquid personal cleansing compositions comprising a cleansing phase and a separate benefit phase wherein the two phases are packaged in physical contact with improved stability.

BACKGROUND OF THE INVENTION

Personal cleansing compositions that attempt to provide skin-conditioning benefits are known. Many of these compositions are aqueous systems comprising an emulsified conditioning oil or other similar materials in combination with a lathering surfactant. Although these products provide both conditioning and cleansing benefits, it is often difficult to formulate a product that deposits sufficient amount of skin conditioning agents on skin during use. In order to combat emulsification of the skin conditioning agents by the cleansing surfactant, large amounts of the skin conditioning agent are added to the compositions. However, this introduces another problem associated with these dual cleansing and conditioning products. Raising the level of skin conditioning agent in order to achieve increased deposition negatively affects product lather performance and stability.

One attempt at providing conditioning and cleansing benefits from a personal cleansing product while maintaining stability has been the use of dual-chamber packaging. These packages comprise separate cleansing compositions and conditioning compositions, and allow for the co-dispensing of the two in a single or dual stream. The separate conditioning and cleansing compositions thus remain physically separate and stable during prolonged storage and just prior to application, but then mix during or after dispensing to provide conditioning and cleansing benefits from a physically stable system. Although such dual-chamber delivery systems provide improved conditioning benefits over the use of conventional systems, it is often difficult to achieve consistent and uniform performance because of the uneven dispensing ratio between the cleansing phase and the conditioning phase from these dual-chamber packages. Additionally, these packaging systems add considerable cost to the finished product.

Accordingly, the need still remains for a personal cleansing composition that provides both cleansing and improved skin conditioning benefits. The need also remains for a personal cleansing composition comprising two phases in physical contact that remain stable for long periods of time.

It is therefore an object of the present invention to provide a striped liquid personal cleansing composition comprising cleansing and benefit phases that are packaged in physical contact while remaining stable, wherein the compositions provide improved deposition of conditioning agents on skin.

It has now been found that a striped liquid personal cleansing composition containing both cleansing and benefit phases that are packaged in physical contact while remaining stable, can be formulated to provide improved cosmetics and skin feel during and after application while also providing excellent skin conditioning and cleansing benefits. It has been found that such a composition can be formulated with sufficiently high levels of benefit agents without compromising product lather performance and stability. Superior lather performance can be demonstrated via the lather volume method described herein.

It has also been found that striped personal cleansing compositions can be formulated with enhanced stability by density matching of the cleansing phase and the benefit phase and by incorporating density modifiers in the cleansing phase and/or the benefit phase.

SUMMARY OF THE INVENTION

The present invention is directed to a striped personal cleansing composition comprising first stripe comprising a cleansing phase comprising a surfactant, water, and optional conventional personal cleansing ingredients and at least one additional stripe comprising a separate benefit phase containing at least about 20% by weight of a hydrophobic material having a Vaughn Solubility Parameter of from about 5 to about 15, wherein the benefit phase has a Consistency Value of from about 1 to about 10,000 poise.

The present invention further relates to a striped liquid personal cleansing composition comprising:

a) a first stripe comprising a cleansing phase comprising from about 1% to about 50% by weight of the cleansing phase of a surfactant selected from the group consisting of anionic surfactant, non-ionic surfactant, zwitterionic surfactant, cationic surfactant, soap and mixtures thereof;

wherein the cleansing phase is non-Newtonian shear thinning, and has a viscosity of equal to or greater than about 3,000 cps and a yield value of at least about 0.1 Pa; and b) a benefit phase comprising from about 20% to about 100% by weight of the benefit phase of a hydrophobic material selected from the group consisting of lipids, hydrocarbons, fats, oils, hydrophobic plant extracts, fatty acids, essential oils, silicone oils, and mixtures thereof;

wherein the hydrophobic material has a Vaughan Solubility Parameter of about 5 to about 15 and further wherein the weight ratio between the cleansing phase and the benefit phase is from about 1:9 to about 99:1 and the cleansing phase and benefit phase are in physical contact in the same package and remain stable in ambient conditions for at least about 180 days; and wherein the cleansing phase and benefit phase are present as stripes wherein the stripe size is at least about 0.1 mm in width and at least about 1 mm in length;

wherein the cleansing phase and/or the benefit phase contains a density modifier to match the cleansing phase density to the benefit phase density.

The present invention further relates to a striped personal cleansing composition comprising a cleansing phase and benefit phase wherein at least one phase contains a colorant, wherein both phases are packed in a single package such that the two phases form a pattern.

The present invention is also directed to a method of cleansing and moisturizing the skin by applying to the skin a composition as described above. These compositions provide improved deposition of skin benefit agents on skin during application.

DETAILED DESCRIPTION

The striped personal cleansing compositions and methods of the present invention comprise personal cleansing compositions comprising a first stripe comprising a cleansing phase and at least one additional stripe comprising a separate benefit phase. These and other essential limitations of the compositions and methods of the present invention, as well as many of the optional ingredients suitable for use herein, are described in detail hereinafter.

The term "anhydrous" as used herein, unless otherwise specified, refers to those compositions or materials containing less than about 10%, more preferably less than about 5%, even more preferably less than about 3%, even more preferably zero percent, by weight of water.

The term "ambient conditions" as used herein, unless otherwise specified, refers to surrounding conditions at one (1) atmosphere of pressure, 50% relative humidity, and 25° C.

The term "stable" as used herein, unless otherwise specified, refers to compositions that maintain at least two "separate" phases in physical contact at ambient conditions for a period of at least about 180 days. By "separate" is meant that there is substantially no mixing, observable to the naked eye, prior to dispensing of the composition.

The term "personal cleansing composition" as used herein, unless otherwise specified, refers to the compositions of the present invention, wherein the compositions are intended to include only those compositions for topical application to the skin or hair, and specifically excludes those compositions that are directed primarily to other applications such as hard surface cleansing, fabric or laundry cleansing, and similar other applications not intended primarily for topical application to the hair or skin.

The Vaughan Solubility Parameter (VSP) as used herein is a parameter used to define the solubility of lipophilic materials. Vaughan Solubility parameters are well known in the various chemical and formulation arts and typically have a range of from 5 to 25.

The term "Consistency" or "k" as used herein is a measure of lipid viscosity and is used in combination with Shear index, to define viscosity for materials whose viscosity is a function of shear. The measurements are made at 35° C. and the units are poise (equal to 100 cps).

The term "Shear index" or "n" as used herein is a measure of lipid viscosity and is used in combination with Consistency, to define viscosity for materials whose viscosity is a function of shear. The measurements are made at 35° C. and the units are dimensionless.

The phrase "substantially free of" as used herein, unless otherwise specified means that the composition comprises less than about 5%, preferably less than about 3%, more preferably less than about 1% and most preferably less than about 0.1% of the stated ingredient.

The term "a striped" personal cleansing composition as used herein, is one that comprises separate phases that form a pattern that is selected from the group consisting of striped, geometric, marbled and mixtures thereof. Preferably, the stripe size is at least about 0.1 mm in width and at least 1 mm in length. More preferably, the stripe size is at least about 0.5 mm in width and at least 10 mm in length. Even more preferably, the stripe size is at least about 1 mm in width and at least 20 mm in length.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The personal cleansing compositions and methods of the present invention can comprise, consist of, or consist essentially of, the essential elements and limitations of the invention described herein, as well as any additional or optional ingredients, components, or limitations described herein or otherwise useful in personal cleansing compositions intended for topical application to the hair or skin.

Product Form

The personal cleansing compositions of the present invention can be in the form of liquid, semi-liquid, cream, lotion or gel compositions intended for topical application to skin. These compositions contain a cleansing phase and a benefit phase, both of which are described in greater detail hereinafter.

All of the product forms contemplated for purposes of defining the compositions and methods of the present invention are rinse-off formulations, by which is meant the product is applied topically to the skin or hair and then subsequently (i.e., within minutes) rinsed away with water, or otherwise wiped off using a substrate or other suitable removal means.

The personal cleansing composition of the present invention preferably has a density in the cleaning phase and a density in the benefit phase that match. Preferably the density matched is about less than 0.15 g/cm$^3$, more preferably less than about 0.1 g/cm$^3$, even more preferably less than 0.05 g/cm$^3$, still even more preferably less than 0.01 g/cm$^3$.

Cleansing Phase

The personal cleansing compositions of the present invention comprise an aqueous cleansing phase that contains a surfactant suitable for application to the skin or hair. Suitable surfactants for use herein include any known or otherwise effective cleansing surfactant suitable for application to the skin, and which is otherwise compatible with the other essential ingredients in the aqueous cleansing phase of the compositions. These cleansing surfactants include anionic, nonionic, cationic, zwitterionic or amphoteric surfactants, or combinations thereof.

The aqueous cleansing phase of the personal care compositions preferably comprises a cleansing surfactant at concentrations ranging from about 1% to about 50%, more preferably from about 4% to about 30%, even more preferably from about 5% to about 25%, by weight of the aqueous cleansing phase. The preferred pH range of the cleansing phase is from about 5 to about 8.

Anionic surfactants suitable for use in the cleansing phase include alkyl and alkyl ether sulfates. These materials have the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohols having from about 8 to about 24 carbon atoms. Preferably, R has from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, preferably from about 3 to about 5, and more preferably with about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the cleansing phase are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula [$R^1$—$SO_3$-M], wherein $R^1$ is chosen from the group consisting of a straight or branched chain, saturated aliphatic hydrocarbon radical having from about 8 to about 24, preferably about 10 to about 18, carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Other suitable surfactants are described in *McCutcheon's, Emulsifiers and Detergents*, 1989 *Annual*, published by M. C. Publishing Co., and in U.S. Pat. No. 3,929,678.

Preferred anionic surfactants for use in the cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Anionic surfactants with branched alkyl chains such as sodium trideceth sulfate, for example, are preferred in some embodiments. Mixtures of anionic surfactants may be used in some embodiments.

Additional surfactant from the classes of amphoteric, zwitterionic surfactant, cationic surfactant, and/or nonionic surfactant may be incorporated in the cleansing phase compositions.

Amphoteric surfactants suitable for use in the cleansing phase include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

Zwitterionic surfactants suitable for use in the cleansing phase include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

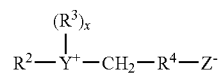

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use in the cleansing phase include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alphacarboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH($CH_2$)$_3$ radical is attached to the nitrogen atom of the betaine are also useful in this invention.

Amphoacetates and diamphoacetates may also be used.

Amphoacetate

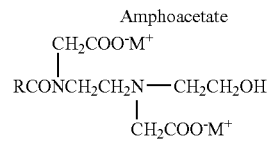

Diamphoacetate

Amphoacetates and diamphoacetates conform to the formulas (above) where R is an aliphatic group of 8 to 18 carbon atoms. M is a cation such as sodium, potassium, ammonium, or substituted ammonium. Sodium lauroamphoacetate, sodium cocoamphoactetate, disodium lauroamphoacetate, and disodium cocodiamphoacetate are preferred in some embodiments.

Cationic surfactants can also be used in the cleansing phase, but are generally less preferred, and preferably represent less than about 5% by weight of the compositions.

Suitable nonionic surfactants for use in the aqueous cleansing phase include condensation products of alkylene oxide groups (hydrophilic in nature) with an organic hydrophobic compound, which may be aliphatic or alkyl aromatic in nature.

Stability Enhancers

Density Modifiers

To further improve stability under stress conditions such as high temperature and vibration, it is preferable to adjust the densities of the separate phases such that they are substantially equal. To achieve this, low density microspheres are added to the cleansing phase of the striped composition. The low density microspheres employed to reduce the overall density of the cleansing phase are particles having a density lower than 0.7 g/cm$^3$, preferably less than 0.2 g/cm$^3$, more preferably less than 0.1 g/cm$^3$, most preferably less than 0.05 g/cm$^3$. The low density microspheres generally have a diameter less than 200 μm, preferably less than 100 μm, most preferably less than 40 μm. Preferably, the density difference between the cleansing phase and the benefit phase is less than 0.15 g/cm$^3$, more preferably, the density difference is less than 0.10 g/cm$^3$, even more preferably, the density difference is less than 0.05 g/cm$^3$, most preferably, the density difference is less than 0.01 g/cm$^3$.

The microspheres are produced from any appropriate inorganic or organic material, compatible with a use on the skin, that is, nonirritating and nontoxic. Preferably, the microspheres don't negatively impact the product lather performance.

Expanded microspheres made of thermoplastic material are known, and may be obtained, for example, according to the processes described in Patents and Patent Applications EP-56219, EP-348372, EP-486080, EP-320473, EP-112807 and U.S. Pat. No. 3,615,972.

These microspheres may be produced from any nontoxic and non-irritant thermoplastic materials. Polymers or copolymers of acrylonitrile or of vinylidene chloride may be used, for example. It is possible to use, for example, a copolymer containing, by weight, from 0 to 60% of units derived from vinylidene chloride, from 20 to 90% of units derived from acrylonitrile and from 0 to 50% of units derived from an acrylic or styrene monomer, the sum of the percentages (by weight) being equal to 100. The acrylic monomer is, for example, a methyl or ethyl acrylate or methacrylate. The styrene monomer is, for example, alpha-methylstyrene or styrene. These microspheres can be in the dry or hydrated state.

The internal cavity of expanded hollow microspheres contains a gas, which can be a hydrocarbon such as isobutane or isopentane or alternatively air. Among hollow microspheres which can be used, special mention may be made of those marketed under the brand name EXPANCEL® (thermoplastic expandable microspheres) by the Akzo Nobel Company, especially those of DE (dry state) or WE (hydrated state) grade. Examples include: Expancel® 091 DE 40 d30; Expancel® 091 DE 80 d30; Expancel® 051 DE 40 d60; Expancel® 091 WE 40 d24; Expancel® 053 DE 40 d20.

Representative microspheres derived from an inorganic material, include, for instance, "Qcel® Hollow Microspheres" and "EXTENDOSPHERES™ Ceramic Hollow Spheres", both available from the PQ Corporation. Examples are: Qcel® 300; Qcel® 6019; Qcel® 6042S.

Just as low density microspheres can be added to the cleansing phase of the present invention to improve vibrational stability, high density materials can be added to the benefit phase to increase its density having the same impact on stability.

Optional Ingredients for Use in the Cleansing Phase

Other suitable optional ingredients in the cleansing phase are one or more humectants and solutes. A variety of humectants and solutes can be employed and can be present at a level of from about 0.1% to about 50%, preferably from about 0.5% to about 35%, and more preferably from about 2% to about 20% of a non-volatile, organic material having a solubility of a least 5 parts in 10 parts water. A preferred water soluble, organic material is selected from the group consisting of a polyol of the structure:

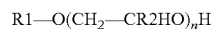

where R1=H, C1-C4 alkyl; R2=H, CH$_3$ and n=1-200; C2-C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D-, L-, and the D,L-forms); pyrrolidone carboxylic acid; hyaluronic acid; lactamide monoethanolamine; acetamide monoethanolamine; urea; and ethanol amines of the general structure (HOCH$_2$CH$_2$)$_x$NH$_y$, where x=1-3; y=0-2, and x+y=3, and mixtures thereof. The most preferred polyols are selected from the group consisting of glycerine, polyoxypropylene(1) glycerol and polyoxypropylene(3) glycerol, sorbitol, butylene glycol, propylene glycol, sucrose, urea and triethanol amine.

Nonionic polyethylene/polypropylene glycol polymers are preferably used as skin conditioning agents. Polymers useful herein that are especially preferred are PEG-2M wherein x equals 2 and n has an average value of about 2,000 (PEG 2-M is also known as Polyox WSR® N-10 from Union Carbide and as PEG-2,000); PEG-5M wherein x equals 2 and n has an average value of about 5,000 (PEG 5-M is also known as Polyox WSR® 35 and Polyox WSR® N-80, both from Union Carbide and as PEG-5,000 and Polyethylene Glycol 200,000); PEG-7M wherein x equals 2 and n has an average value of about 7,000 (PEG 7-M is also known as Polyox WSR® (N-750 from Union Carbide); PEG-9M wherein x equals 2 and n has an average value of about 9,000 (PEG 9-M is also known as Polyox WSR® N-3333 from Union Carbide); PEG-14 M wherein x equals 2 and n has an average value of about 14,000 (PEG 14-M is also known as Polyox WSR-205 and Polyox WSR® N-3000 both from Union Carbide); and PEG-90M wherein x equals 2 and n has an average value of about 90,000 (PEG-90M is also known as Polyox WSR®-301 from Union Carbide.)

Other non limiting examples of these optional ingredients include vitamins and derivatives thereof (e.g., ascorbic acid, vitamin E, tocopheryl acetate, and the like); sunscreens; thickening agents (e.g., polyol alkoxy ester, available as Crothix from Croda); preservatives for maintaining the anti microbial integrity of the cleansing compositions; anti-acne medicaments (resorcinol, salicylic acid, and the like); anti-oxidants; skin soothing and healing agents such as aloe vera extract, allantoin and the like; chelators and sequestrants; and agents suitable for aesthetic purposes such as fragrances, essential oils, skin sensates, pigrnents, pearlescent agents (e.g., mica and titanium dioxide), lakes, colorings, and the like (e.g., clove oil, menthol, camphor, eucalyptus oil, and eugenol).

Non limiting examples of suitable carboxylic copolymers, emulsifiers, emollients, and other additional ingredients are disclosed in U.S. Pat. No. 5,011,681, to Ciotti et al., issued Apr. 30, 1991.

Without wishing to be bound by theory, it is believed that in some examples the compositions of the invention may have a lamellar structure. The compositions of the invention have free-flowing Non-Newtonian shear-thinning properties and the ability to suspend components (which are known characteristics of lamellar phase surfactant compositions).

In another preferred embodiment of the present invention the surfactant compositions for use in the cleansing phase exhibiting Non-Newtonian shear thinning behavior (herein referred to as free flowing compositions). These surfactant compositions comprise water, at least one anionic surfactant, an electrolyte and at least one alkanolamide. It has been found that by employing a cleansing phase exhibiting Non-Newtonian shear thinning behavior, the stability of the resulting personal cleansing composition may be increased.

The alkanolamide if present has the general structure of:

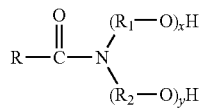

wherein R is $C_8$ to $C_{24}$ or preferably in some embodiments $C_8$ to $C_{22}$ or in other embodiments $C_8$ to $C_{18\ saturated}$ or unsaturated straight chain or branched aliphatic group, $R_1$ and $R_2$ are the same or different $C_2$-$C_4$ straight chain or branched aliphatic group, x=0 to 10; y=1-10 and wherein the sum of x and y is less than or equal to 10.

The amount of alkanolamide in the composition is typically about 0.1% to about 10% by weight, and in some embodiments is preferably about 2% to about 5% by weight of the cleansing phase. Some preferred alkanolamides include Cocamide MEA (Coco monethanolamide) and Cocamide MIPA (Coco monoisopropranolamide).

The electrolyte, if used, can be added per se to the composition or it can be formed in situ via the counter-ions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium or ammonium chloride or sodium or ammonium sulfate.

The electrolyte, when present, should be present in an amount, which facilitates formation of the free flowing composition. Generally, this amount is from about 0.1% by weight to about 15% by weight, preferably from about 1% to about 6% by weight of the cleansing phase, but may be varied if required.

Frequently surfactants are sold as solutions in water or other solvents which dilute them to less than 100% active surfactant, therefore the "active surfactant" means actual amount of surfactant delivered to the free flowing composition from a commercial surfactant preparation.

The total amount of all surfactants e.g. anionic surfactants, nonionic surfactants, amphoteric and/or zwitterionic surfactants, and cationic surfactants taken together, is typically about 8 to about 30% active surfactant and preferably about 10 to about 20% active surfactant. In some embodiments it is preferable that at least one of the surfactants has an aliphatic chain that has branching or unsaturation or a combination thereof.

Viscosity of Cleansing Phase Composition

The Wells-Brookfield Cone/Plate Model DV-II+ can be used to determine the viscosity of the personal cleansing composition described herein. The determination is performed at 25° C. with 2.4 cm 3° cone measuring system with a gap of 0.013 mm between the two small pins on the respective cone and plate. The measurement is performed by injecting 0.5 ml. of the sample to be analyzed between the cone and the plate and toting the cone at a set speed of 1 rpm. The resistance to rotation of the cone produces a torque that is proportional to the shear stress of the liquid sample. The amount of torque is read and computed by the viscometer into absolute centipoises units (cps) based on geometric constant of the cone, the rate of rotation, and the stress related torque.

Preferably, the cleansing phase has a viscosity of greater than 3,000 cps. More preferably, the viscosity is greater than 5,000 cps. Even more preferably, the viscosity is greater than 10,000 cps. Most preferably, the viscosity is greater than 20,000 cps.

Yield Point of Cleansing Phase Composition

The Carrimed CSL 100 Controlled Stress Rheometer can be used to determine the yield point of the personal cleansing composition described herein. For purposes herein, the yield point is the amount of stress required to produce a strain of 1% on the personal cleansing composition. The determination is performed at 25° C. with the 4 cm 2° cone measuring system set with a 51 micron gap. The determination is performed via the programmed application of shear stress (typically from about 0.06 dynes/sq. centimeter to about 500 dynes/sq. centimeter) over time. This amount of stress results in a deformation of the sample. A shear stress versus strain curve can be created. From this curve, the yield point of the personal cleansing composition can be calculated.

Preferably, the cleansing phase has a yield point of greater than 0.1 Pascal. More preferably, the yield point is greater than 1 Pascal. Even more preferably, the yield point is greater than 10 Pascal. Most preferably, the yield point is greater than 30 Pascal.

Benefit Phase

The separate benefit phase in the present invention is preferably anhydrous. The benefit phase comprises from about 20% to about 100%, preferably at least about 35%, most preferably at least about 50% of a hydrophobic skin benefit agent. In an embodiment, the benefit phase is substantially free of surfactants. The benefit agents suitable for use in the present invention have a Vaughan Solubility Parameter of from about 5 to about 15. The benefit agents are preferably selected among those having defined rheological properties as described hereinafter, including selected Consistency (k) and Shear Index (n). These preferred rheological properties are especially useful in providing the personal cleansing compositions with improved deposition of benefit agents on skin.

Vaughan Solubility Parameter Value (VSP)

The hydrophobic skin benefit agent for use in the benefit phase of the composition has a Vaughan Solubility Parameter (VSP) of from about 5 to about 15 $(cal/cm^3)^{0.5}$, preferably from about 6 to less than 10 $(cal/cm^3)^{0.5}$, more preferably from about 6 to about 9 $(cal/cm^3)^{0.5}$. These solubility parameters are well known in the formulation arts, and are defined by Vaughan in *Cosmetics and Toiletries*, Vol. 103, p47-69, October 1988.

Non-limiting examples of hydrophobic skin benefit agent having VSP values ranging from about 5 to about 15$(cal/cm^3)^{0.5}$ include the following:

VAUGHAN SOLUBILITY PARAMETERS*$(cal/cm^3)^{0.5}$

| VAUGHAN SOLUBILITY PARAMETERS* | |
|---|---|
| Cyclomethicone | 5.92 |
| Squalene | 6.03 |
| Petrolatum | 7.33 |
| Isopropyl Palmitate | 7.78 |
| Isopropyl Myristate | 8.02 |
| Castor Oil | 8.90 |
| Cholesterol | 9.55 |

*As reported in Solubility, Effects in Product, Package, Penetration and Preservation, C.D. Vaughan, Cosmetics and Toiletries, Vol. 103, October 1988.

B) Rheology

The hydrophobic skin benefit agents for use in the benefit phase of the composition have a preferred rheology profile as defined by Consistency (k) and Shear Index (n). Preferred Consistency ranges are 1-10,000 poise $(1/sec)^{n-1}$, preferably 10-2000 poise $(1/sec)^{n-1}$ and more preferably 50-1000 poise $(1/sec)^{n-1}$. Shear Index ranges are 0.1-0.8, preferably 0.1-0.5 and more preferably 0.20-0.4.

The hydrophobic skin benefit agents can be characterized by Consistency (k) and Shear Index (n) values as defined by the above-described ranges, wherein these defined ranges are selected to provide enhanced deposition and reduced stickiness during and after application of the personal cleaning composition on hair or skin.

The Shear index (n) and Consistency (k) values are well known and accepted industry standards for reporting the viscosity profile of materials having a viscosity that is a function of an applied shear rate.

The viscosity ($\mu$) for any material can be characterized by the relationship or equation $$\mu = \sigma/\gamma'$$

wherein $\sigma$ is shear stress and $\gamma'$ is shear rate, so that the viscosity for any material can be measured by either applying a shear rate and measuring the resultant shear stress or vice versa.

The Carrimed CSL 100 Controlled Stress Rheometer is used to determine Shear Index, n, and Consistency, k, for the hydrophobic skin benefit agents herein. The determination is performed at 35° C. with the 4 cm 2° cone measuring system typically set with a 51 micron gap and is performed via the programmed application of a shear stress (typically from about 0.06 dynes/sq. cm to about 5,000 dynes/sq. cm) over time. If this stress results in a deformation of the sample, i.e. strain of the measuring geometry of at least 10-4 rad/sec, then this rate of strain is reported as a shear rate. These data are used to create a viscosity ($\mu$) versus shear rate ($\gamma'$) flow curve for the hydrophobic skin benefit agent material. This flow curve can then be modeled in order to provide a mathematical expression that describes the material's behavior within specific limits of shear stress and shear rate. These results are fitted with the following well-accepted power law model (see for instance: *Chemical Engineering*, by Coulson and Richardson, Pergamon, 1982 or *Transport Phenomena* by Bird, Stewart and Lightfoot, Wiley, 1960):

$$\mu = k\,(\gamma')^{n-1}$$

The Carrimed CSL 100 Controlled Stress Rheometer is used to perform oscillatory tests at 35° C. with the 4 cm 2° cone measuring system typically set with a 51 micron gap. The oscillatory tests at 35° C. are carried out in 2 steps. The first step is a stress amplitude sweep at the expected starting and ending frequencies for the frequency sweep. These tests allow a determination to be made as to whether or not the test conditions are within the linear viscoelastic region for the test material over the anticipated frequency range. The linear viscoelastic region is a region where there is a linear relationship between stress and strain. The second step is a frequency sweep made at a stress level within that linear viscoelastic region. The frequency sweep allows the test material's viscoelastic behavior to be measured. The oscillatory test on a controlled stress rheometer is performed by applying a stress in an oscillatory manner and measuring the resulting oscillatory strain response and the phase shift between the applied stress wave form and the resulting strain wave form in the test material. The resulting complex modulus is expressed as a combination of the material's elastic (G') and viscous (G") components. The elastic modulus G' is a measure of a materials ability to store recoverable energy. This energy storage can be the result of the ability of a complex polymer, structural network, or a combination of these to recover stored energy after a deformation. The viscous or loss modulus G" is a measure of the unrecoverable energy, which has been lost due to viscous flow.

The hydrophobic skin benefit agents suitable for use herein can include a variety of hydrocarbons, oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin and its derivatives, wax esters, beeswax derivatives, sterols and phospholipids, and combinations thereof.

Non-limiting examples of hydrocarbon oils and waxes suitable for use herein include petrolatum, mineral oil, microcrystalline waxes, polyalkenes, paraffins, cerasin, ozokerite, polyethylene, perhydrosqualene, and combinations thereof.

Non-limiting examples of silicone oils suitable for use as hydrophobic skin benefit agents herein include dimethicone copolyol, dimethylpolysiloxane, diethylpolysiloxane, mixed $C_1$-$C_{30}$ alkyl polysiloxanes, phenyl dimethicone, dimethiconol, and combinations thereof. Preferred are non-volatile silicones selected from dimethicone, dimethiconol, mixed $C_1$-$C_{30}$ alkyl polysiloxane, and combinations thereof. Non-limiting examples of silicone oils useful herein are described in U.S. Pat. No. 5,011,681 (Ciotti et al.).

Non-limiting examples of diglycerides and triglycerides suitable for use as hydrophobic skin benefit agents herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof.

Non-limiting examples of acetoglyceride esters suitable for use as hydrophobic skin benefit agents herein include acetylated monoglycerides.

Non-limiting examples of alkyl esters suitable for use as hydrophobic skin benefit agents herein include isopropyl esters of fatty acids and long chain esters of long chain (i.e. $C_{10}$-$C_{24}$) fatty acids, e.g. cetyl ricinoleate, non-limiting examples of which incloude isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as hydrophobic skin benefit agents herein include oleyl myristate, oleyl stearate, oleyl oleate, and combinations thereof.

Non-limiting examples of lanolin and lanolin derivatives suitable for use as hydrophobic skin benefit agents herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Still other suitable hydrophobic skin benefit agents include milk triglycerides (e.g., hydroxylated milk glyceride) and polyol fatty acid polyesters.

Still other suitable hydrophobic skin benefit agents include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

The benefit phase of the composition preferably comprises one or more hydrophobic skin benefit agents, wherein at least 20% by weight of the hydrophobic skin benefit agents are selected from petrolatum, mineral oil, sunflower seed oil, micro-crystalline waxes, paraffins, ozokerite, polyethylene, polybutene, polydecene and perhydrosqualene dimethicones, cyclomethicones, alkyl siloxanes, polymethylsiloxanes and methylphenylpolysiloxanes, lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, castor oil, soy bean oil, maleated soy bean oil, safflower oil, cotton seed oil, corn oil, walnut oil, peanut oil, olive oil, cod liver oil, almond oil, avocado oil, palm oil and sesame oil, and combinations thereof. More preferably, at least about 50% by weight of the lipophilic skin conditioning agents are selected from the groups of petrolatum, mineral oil, paraffins, polyethylene, polybutene, polydecene, dimethicones, alkyl siloxanes, cyclomethicones, lanolin, lanolin oil, lanolin wax. The remainder of the lipophilic skin conditioning agent is preferably selected from: isopropyl palmitate, cetyl riconoleate, octyl isononanoate, octyl palmitate, isocetyl stearate, hydroxylated milk glyceride and combinations thereof.

Stability Enhancers

Structurants

The benefit phase of the striped personal cleansing composition can comprise a structurant, which improves the high temperature stability of the composition. Preferred structurants suitable that can be used in the present invention include those structurants that are immiscible in the aqueous cleansing phase and may take the form of a wax, hydrophobic silica, hydrophobic clay, polymer or mixtures thereof. In one embodiment of the present invention, the structurant can comprise a crystalline, hydroxyl-containing stabilizer. Tri-hydroxystearin is most preferred. Tri hydroxystearin is available commercially as Thixcin R from Rheox and as Flowtone from Southern Clay Products.

Additionally, the structurant can comprise hydrophobically modified dispersed amorphous silica. As used herein the term "dispersed amorphous silica" refers to small, finely divided non-crystalline silica having a mean agglomerate particle size of less than about 100 microns.

Fumed silica, is produced by the vapor phase hydrolysis of silicon tetrachloride in a hydrogen oxygen flame. It is believed that the combustion process creates silicone dioxide molecules which condense to form particles.

The particles collide, attach and sinter together. The result of this process is a three dimensional branched chain aggregate. Once the aggregate cools below the fusion point of silica, which is about 1710° C., further collisions result in mechanical entanglement of the chains to form agglomerates. Precipitated silicas and silica gels are generally made in aqueous solution. See, Cabot Technical Data Pamphlet TD-100 entitled "CAB-O-SIL@ Untreated Fumed Silica Properties and Functions", October 1993, and Cabot Technical Data Pamphlet TD-104 entitled "CAB-O-SIL@ Fumed Silica in Cosmetic and Personal Care Products", March 1992.

The fumed silica preferably has a mean agglomerate particle size ranging from about 0.1 microns to about 100 microns, more preferably from about 1 micron to about 50 microns, and more preferably still from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and more preferably still from about 0.2 microns to about 0.3 microns. The silica preferably has a surface area greater than 50 sq. m/gram, more preferably greater than about 130 sq. m/gram, and more preferably still greater than about 180 sq. m./gram.

The fumed silica is hydrophobically modified via the addition of non-polar moieties to the surface of the silica. Exemplary hydrophobically modified fumed silicas for use in the present invention include, but are not limited to, silica dimethyl silylate whereby the surface of the fumed silica has been modified with dimethyl silyl groups available commercially as Aerosil R972 and Aerosil R974 both available from Degussa; and CAB-O-SIL TS-610 and CAB-O-SIL TS-720 both available from Cabot- and silica silylate whereby the surface of the fumed silica has been modified with trimethylsiloxyl groups available commercially as Aerosil R812 and Sipemat D17 both available from Degussa- and CAB SIL TS-530 available from Cabot.

Additionally, the structurant can comprise hydrophobically modified dispersed smectite clay selected from the group consisting of bentonite, hectorite and mixtures thereof. Bentonite is a colloidal aluminum clay sulfate. See Merck Index, Eleventh Edition, 1989, entry 1062, p. 164. Hectorite is a clay containing sodium, magnesium, lithium, silicon, oxygen, hydrogen and fluorine. See Merck Index, Eleventh Edition, 1989, entry 4538, p. 729.

Hyrophobically modified dispersed smectite clays are called organoclays and are formed by reacting monoquaternary compounds with the smectite clays to form an organoclay complex. Non-limiting examples of organoclays for use in the present invention include dihydrogenated tallow benzylmonium hectorite available commercially as Bentone SD-3 from Rheox; quaternium-18 hectorite available commercially as Bentone and in mixtures M-P-A 14, Bentone Gel DOA, Bentone Gel ECO 5, Bentone Gel EUG, Bentone Gel IPP, Bentone Gel ISD, Bentone Gel MIO, Bentone Gel MIO- A40, Bentone Gel SS-71, Bentone Gel 10ST, Bentone Gel VS-5, Bentone Gel VS-8, Bentone Gel VS-38, Bentone Gel VS-5PC, and Bentone Gel YVS all available from Rheox, quaternium-18 bentonite available commercially as Bentone 34 from Rheox and Claytone 40 and Claytone SO from Southern Clay- quatemium-18/benzalkonium bentonite available commercially as Claytone HT from Southern Clay-stearalkonium bentonite available commercially as Claytone AF from Southern Clay, Toxogel LG and Tixogel VZ from United Catalysts, and Viscogel B7 from Bentec- and stearalkonium hectorite available commercially as Bentone 27 from Rheox and in mixtures Bentone Gel CAO, Bentone Gel IPM, Bentone Gel LOI, Bentone Gel M-20, Bentone Gel RSS, Bentone Gel SIL, and Bentone Gel TN, all from Rheox.

The structurant can also comprise the use of metal soaps, homopolymers, ionic homo- and copolymers and block copolymers. Some common gelling agents which can be used in the present invention include fatty acid soaps of lithium, calcium, sodium, aluminum, zinc and barium. A number of homo-and copolymers can also be used including atactic ethylenepropylene. Homopolymers or copolymers which have pendant salt groups also form ion rich aggregates in a non-polar matrix. The ionic interaction and resultant polymer properties of these compositions, however, are dependent on the type of polymer backbone, type of ionic moiety and type of cation. Sulfonated polystyrenes exemplify this kind of system. Block systems used in the present invention include styrene-isoprene, styrene-butadiene and styrene ethylene oxide copolymers.

Commercially available thermoplastic rubber type polymers are especially useful as structurants in the benefit phase. They are sold under the trademark Kraton® by Shell Chemical Company. The Kraton® rubber polymers are described as elastomers which have an unusual combination of high strength and low viscosity and a unique molecular structure of linear diblock, triblock and radial polymers. Each molecule of the Kraton® rubber is said to consist of block segments of styrene monomer units and rubber monomer units. Each block segment may consist of 100 monomer units or more. The most common structure is the linear ABA block type; styrene-butadiene-styrene (SBS) and styrene-isoprene-styrene (SIS), the Kraton® D rubber series. A second generation polymer of this series is the Kraton® G series which are styrene-ethylene-butylene-styrene type (S-EB-S) polymers. Diblock polymers include the ABA type and the SB, styrene-ethylene-propylene (S-EP) and (S-EB). The ABA structure of the Kraton® rubber molecule has polystyrene endblocks and elastomeric midblocks. Examples of Kroton® are G1701, G1702, D1107, D1111, D1320 available from Shell Company. It is preferred that blends of di- and triblock copolymers are used as benefit phase structurants in the present invention. Gelled hydrocarbon oils using blends of di- and triblock copolymers are commercially available from Penreco under the tradename Versagel. For example, Versagel M is a gelled mineral oil base, Versagel ME is a gelled hydrogenated polyisobutene base, Versagel MP is a gelled isopropyl palmitate base, Versagel MC is a gelled isohexadecane base, and Versagel MD is a gelled isododecane base.

When present he benefit phase typically contains structurants in an amount of from about 0.01% to about 30%, more preferably from about 0.1% to about 20%, and more preferably still from about 1% to about 10%, based on the weight of the benefit phase.

The separate benefit phase of the striped liquid personal cleansing compositions may optionally comprise the following skin benefit ingredients for enhanced delivery of these benefit materials on skin. Preferred concentrations of optional ingredients range from about 0.1% to about 10%, more preferably from about 0.2% to about 5%, even more preferably from about 0.5% to about 4%, by weight of the personal cleansing composition.

Suitable optional ingredients include but are not limited to desquamation actives, anti-acne actives, anti-wrinkle/anti-atrophy actives, anti-oxidants or radical scavengers, chelating agents, flavonoids, anti-inflammatory agents, anti-cellulite agents, topical anesthetics, tanning agents, skin lightening agents, skin soothing or skin healing actives, antimicrobial actives, sunscreen actives, and solid particulates.

The personal cleansing compositions of the present invention may further comprise other optional ingredients that may modify the physical, chemical, cosmetic or aesthetic characteristics of the compositions or serve as additional "active" components when deposited on the skin. The compositions may also further comprise optional inert ingredients. Many such optional ingredients are known for use in personal care compositions, and may also be used in the personal cleansing compositions herein, provided that such optional materials are compatible with the essential materials described herein, or do not otherwise unduly impair product performance. An example of an optional ingredient is a cationic deposition polymer.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. These optional materials can be used in any aspect of the compositions of the present invention, including either of the active or cleansing phases as described herein.

Optional ingredients for use in the cleansing phase of the compositions of the present invention can include any benefit phase material as described herein that is also compatible with the selected ingredients in the cleansing phase. Likewise, optional ingredients for use in the benefit phase of the compositions of the present invention can include any cleansing phase material described herein that is also compatible with the selected ingredients in the benefit phase.

Other optional ingredients for use in either phase of the composition, preferably the benefit phase, include silicone elastomer powders and fluids to provide any of a variety of product benefits, including improved product stability, application cosmetics, emolliency, conditioning, and so forth. The concentration of the silicone elastomers in the composition preferably ranges from about 0.1% to about 20%, more preferably from about 0.5% to about 10%, by weight of the composition. In this context, the weight percentages are based upon the weight of the silicone elastomers material itself, excluding any silicone-containing fluid that typically accompanies such silicone elastomers materials in the formulation process. The silicone elastomers suitable for optional use herein include emulsifying and non-emulsifying silicone elastomers, non-limiting examples of which are described in U.S. Ser. No. 09/613,266 (assigned to The Procter & Gamble Company).

Density Modifiers

Just as low density microspheres can be added to the cleansing phase of the present invention to improve stability, high density materials can be added to the benefit phase to increase its density having the same impact on stability. The high density particles employed to increase the overall density of the benefit phase are particles having a density greater than 1.1 g/cm$^3$, preferably greater than 1.5 g/cm$^3$, more preferably greater than 2.0 g/cm$^3$, most preferably greater than 2.5 g/cm$^3$. The high density particles generally have a diameter less than 200 μm, preferably less than 100 μm, most preferably less than 40 μm. Preferably, the high density particles are selected from water-insoluble inorganic materials, metals, metal oxides, metal alloys and mixture thereof. Non-limiting examples include calcium carbonate, silica, clays, mica, talc, iron, zinc, copper, lead, titanium dioxide, zinc oxide, and the like.

Method of Use

The striped personal cleansing compositions of the present invention are preferably applied topically to the desired area of the skin or hair in an amount sufficient to provide effective delivery of the skin conditioning agent to the applied surface, or to otherwise provide effective skin conditioning benefits. The compositions can be applied directly to the skin or indirectly via the use of a cleansing puff, washcloth, sponge or other implement. The compositions are preferably diluted with water prior to, during, or after topical application, and then subsequently rinsed or wiped off of the applied surface, preferably rinsed off of the applied surface using water or a water-insoluble substrate in combination with water.

If the personal cleansing compositions contain stripes of varying colors it may be desirable to package these compositions in a transparent package such that the consumer can view the pattern through the package. Because of the viscosity of the subject compositions it may also be desirable to include instructions to the consumer to store the package upside down, on its cap to facilitate dispensing.

The present invention is therefore also directed to methods of cleansing the skin through the above-described application of the compositions of the present invention. The methods of the present invention are also directed to a method of providing effective delivery of the desired skin active agent, and the resulting benefits from such effective delivery as described herein, to the applied surface through the above-described application of the compositions of the present invention.

Method of Manufacture

The personal cleansing compositions of the present invention may be prepared by any known or otherwise effective technique, suitable for making and formulating the desired striped product form. It is especially effective to combine toothpaste-tube filling technology with a spinning stage design. Specific non-limiting examples of such methods as they are applied to specific embodiments of the present invention are described in the following examples.

Lather Volume

Lather volume of a striped liquid personal cleansing composition is measured using a graduated cylinder and a tumbling apparatus. A 1,000 ml graduated cylinder is chosen which is marked in 10 ml increments and has a height of 14.5 inches at the 1,000 ml mark from the inside of its base (for example, Pyrex No. 2982). Distilled water (100 grams at 23° C.) is added to the graduated cylinder. The cylinder is clamped in a rotating device which clamps the cylinder with an axis of rotation that transects the center of the graduated cylinder. One gram of the total personal cleansing composition (0.5 g of the cleansing phase and 0.5 g of the benefit phase) is added into the graduated cylinder and the cylinder is capped. The cylinder is rotated at a rate of 10 revolutions in about 20 seconds, and stopped in a vertical position to complete the first rotation sequence. A timer is set to allow 30 seconds for the lather thus generated to drain. After 30 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). One minute after the first rotation is completed, a second rotation sequence is commenced which is identical in speed and duration to the first rotation sequence. The second lather volume is recorded in the same manner as the first, after the same 30 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume. Compositions according to the present invention perform significantly better in this test than similar compositions in conventional emulsion form.

Density (Specific Gravity) Method

The metal pycnomoeter is utilized for determination of density (specific gravity) of both the surfactant phase and the benefit phase compositions. One suggested type of metal pycnometer can be obtained from Fisher, 3-347. Other equivalent pycnometer can also be used. Following procedure are the steps for measuring density (specific gravity) of the cleansing phase and the benefit phase compositions.

Step 1) Cleaning:

The metal pycnometer must be clean and dry before use. Diassemble the metal pycnometer completely and wash all parts well with water. Follow the water rinse with an alcohol rinse. Expel the alcohol with a stream of dry, clean air.

Step 2) Standardization

Fill the clean, dry pycnometer with distilled water at 25 C. Place the lid on body of pycnometer and screw the cap firmly in place. Dry the outside of pycnometer well with a tissue and weigh to 0.001 g. Clean and dry the pycnometer according to the directions shown above. Assemble and weigh the dry pycnometer to 0.001 g.

Water weight=Weight of pycnometer and water− weight of empty pycnometer

Step 3) Sample Measurement

Clean and dry the pycnometer according to the directions shown above. Allow the sample to equilibrate to room temperature. Pour the sample into the pycnometer, taking care to avoid introducing air into the sample in the pycnometer. Add an excess of sample so that it extends slightly above the top of the threads. Place the lid inside the cap and screw the cap firmly onto the body of the pycnometer. Any excess sample will be forced through the hole in the lid of the pycnometer. Wipe away the excess sample carefully with a tissue. Weight the filled pycnometer to 0.001 g.

Sample Weight=Weight of pycnometer and sample− weight of pycnometer.

Step 4) Specific Gravity=Weight of Sample/Weight of Water

The density difference between the cleansing phase and the benefit phase is less than 0.15 g/cm$^3$, preferably, the density difference is less than 0.10 g/cm$^3$, more preferably, the density difference is less than 0.05 g/cm$^3$, most preferably, the density difference is less than 0.01 g/cm$^3$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Each of the exemplified compositions provides improved deposition or effectiveness of the skin conditioning agents or optional ingredients delivered from each prepared composition.

Examples 1-3

The following examples described in Table 1 are non-limiting examples of cleansing phase and benefit phase compositions.

TABLE 1

Cleansing Phase and Benefit phase Compositions

| Ingredient | Example 1 wt % | Example 2 wt % | Example 3 Wt % |
| --- | --- | --- | --- |
| I. Cleansing Phase Composition | | | |
| Ammonium Laureth-3 Sulfate | 3.0 | 3.0 | 3.0 |
| Sodium Lauroamphoacetate (Miranol L-32 Ultra from Rhodia) | 16.7 | 16.7 | 16.7 |
| Ammonium Lauryl Sulfate | 1.0 | 1.0 | 1.0 |
| Lauric Acid | 0.9 | 0.9 | 0.9 |
| Trihydroxystearin (Thixcin R) | 2.0 | 2.0 | 2.0 |
| Guar Hydroxypropyltrimonium Chloride (N-Hance 3196 from Aqualon) | 0.17 | 0.75 | 0.75 |
| Guar Hydroxypropyltrimonium Chloride (Jaguar C-17 from Rhodia) | 0.58 | — | — |
| Polyquaterium 10 (UCARE polymer JR-30M from Amerchol) | 0.45 | — | — |
| Polymethacrylamidopropyltrimonium Chloride (Polycare 133 from Rhodia) | — | 0.24 | — |
| Polyquaternium-39 (Merqurt Plus 3300 from Calgon) | — | 0.81 | — |
| PEG 90M (Polyox WSR 301 from Union Carbide) | 0.25 | — | — |
| PEG-14M (Polyox WSR N-3000 H from Union Carbide) | 0.45 | 2.45 | 2.45 |
| Linoleamidoprypyl PG-Dimonium Chloride Phosphate Dimethicone (Monasil PLN from Uniqema) | — | 1.0 | 4.0 |
| Glycerin | 1.4 | 4.9 | 4.9 |
| Sodium Chloride | 0.3 | 0.3 | 0.3 |
| Sodium Benzoate | 0.25 | 0.25 | 0.25 |
| Disodium EDTA | 0.13 | 0.13 | 0.13 |
| Glydant | 0.37 | 0.37 | 0.37 |
| Citric Acid | 1.6 | 0.95 | 0.95 |
| Titanium Dioxide | 0.5 | 0.5 | 0.5 |
| Perfume | 0.5 | 0.5 | 0.5 |
| Expancel 091 DE 40 d30 (from Expancel, Inc.) | 0.4 | 0.4 | 0.4 |
| Water | Q.S. | Q.S. | Q.S. |
| II. Benefit phase Composition | | | |
| Petrolatum (SuperWhite Protopet from WITCO) | 75 | 99.92 | 90 |
| Mineral Oil (Hydrobrite 1000 PO White MO from WITCO) | 24.92 | — | 9.92 |
| Pigment | 0.08 | 0.08 | 0.08 |

The compositions described above can be prepared by conventional formulation and mixing techniques. Prepare the cleansing composition 1 by first creating the following premixes: citric acid in water premix at 1:3 ratio, Guar polymer premix with Jaguar C-17 and N-Hance 3196 in water at 1:10 ratio, UCARE premix with JR-30M in water at about 1:30 ratio, and Polyox premix with PEG-90M and PEG-14M in Glycerin at about 1:2 ratio. Then, add the following ingredients into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, UCARE premix, Polyox Premix, and the rest of water. Heat the vessel with agitation until it reaches 190° F. (88° C.). Mix for about 10 min. Cool the batch with a cold water bath with slow agitation until it reaches 110° F. (43° C.). Add the following ingredients: Glydant, perfume, Titanium Dioxide, Expancel. Keep mixing until a homogeneous solution forms.

Prepare the cleansing composition 2 by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, add the following ingredients into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Polycare 133, Merquat Plus 3300, Monosil PLN, and the rest of water. Heat the vessel with agitation until it reaches 190° F. (88° C.). Mix for about 10 min. Cool the batch with a cold water bath with slow agitation until it reaches 110° F. (43° C.). Add the following ingredients: Glydant, perfume, Titanium Dioxide, Expancel. Keep mixing until a homogeneous solution forms.

Prepare the cleansing composition 3 by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, add the following ingredients into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Monasil PLN, and the rest of water. Heat the vessel with agitation until it reaches 190° F. (88° C.). Mix for about 10 min. Cool the batch with a cold water bath with slow agitation until it reaches 110° F. (43° C.). Add the following ingredients: Glydant, perfume, Titanium Dioxide, Expancel. Mix until a homogeneous solution forms.

Prepare the benefit phase, add petrolatum into a mixing vessel. Heat the vessel to 140° F. (60° C.). Then, add mineral oil and cosmetic pigment with agitation. Let the vessel cool down with slow agitation.

The cleansing and benefit phases are density matched to within 0.05 g/cm³. Package both phases into a single container using conventional toothpaste-tube filler equipment. The sample stage spins the bottle during the filling process to create a striped appearance. The stripe size is about 6 mm in width and 100 mm in length.

Examples 4-6

The following examples described in Table 2 are non-limiting examples of cleansing phase and benefit phase compositions of the present invention.

Prepare the compositions described above by conventional formulation and mixing techniques. Prepare the cleansing phase composition by first adding citric acid into water at 1:3 ratio to form a citric acid premix. Then, add the following ingredients into the main mixing vessel in the following sequence: water, Miracare SLB-365, sodium chloride, sodium benzoate, Disodium EDTA, glydant. Start agitation of the main mixing vessel. In a separate mixing vessel, disperse polymers (Polyquaterium 10, Jaguar C-17, or N-Hance 3196) in water at 1:10 ratio and form a polymer premix. Add the completely dispersed polymer premix into the main mixing vessel with continuous agitation. Disperse Polyox WSR 301 in water1 and then add to the main mixing vessel. Then, add the rest of the water, perfume, and Expancel into the batch. Keep agitation until a homogenous solution forms.

Prepare the benefit phase by adding petrolatum into a mixing vessel. Heat the vessel to 190° F. Then, add mineral oil, Bentone Gel, Kraton polymer, or Claytone HY with agitation. High shear the samples containing Bentone Gel or Claytone. Add cosmetic pigment and let the vessel cool down with slow agitation.

The cleansing and benefit phases are density matched to within 0.05 g/cm³. Package both phases into a single container using conventional toothpaste-tube filler equipment. The sample stage spins the bottle during filling process to create a striped appearance. The stripe size is about 6 mm in width and 100 mm in length.

Examples 7-9

The following examples described in Table 3 are non-limiting examples of cleansing phase and benefit phase compositions of the present invention.

TABLE 2

Cleansing Phase and Benefit phase Compositions

| Ingredient | Example 4 wt % | Example 5 wt % | Example 6 wt % |
| --- | --- | --- | --- |
| I. Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Polyquaterium 10 (UCare KG-30M) | 0.7 | — | — |
| Jaguar C-17 (from Rhodia) | — | 0.7 | — |
| Guar Hydroxypropyltrimonium Chloride (N-Hance 3196 from Aqualon) | — | — | 0.7 |
| PEG 90M (Polyox WSR 301 from Dow Chemical) | — | — | 0.2 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Expancel 091 DE 40 d30 (from Expancel, Inc.) | 0.4 | 0.4 | 0.4 |
| Water | Q.S. | Q.S. | Q.S. |
| (pH) | (6.0) | (6.0) | (6.0) |
| II. Benefit phase Composition | | | |
| Petrolatum (Superwhite Protopet from WITCO) | 75 | 75 | 75 |
| Bentone Gel MIO (from Rheox) | 24.92 | — | — |
| Mineral Oil (Hydrobrite 1000 PO White MO from WITCO) | — | 23.92 | 23.92 |
| Kraton G1702 (from Shell) | — | 1 | — |
| Claytone HY (from Southern Clay) | — | — | 1 |
| Colorona Magenta Cosmetic Pigment (from Rona) | 0.08 | 0.08 | 0.08 |

TABLE 3

Cleansing Phase and Benefit phase Compositions

| Ingredient | Example 7 wt % | Example 8 wt % | Example 9 wt % |
|---|---|---|---|
| I. Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Expancel 091 DE40 d30 (from Expancel, Inc.) | 0.4 | 0.4 | 0.4 |
| Water | Q.S. | Q.S. | Q.S. |
| (pH) | (6.0) | (6.0) | (6.0) |
| II. Benefit phase Composition | | | |
| Versagel M500 (Gelled Mineral Oil from Penreco) | 99.92 | — | — |
| Versagel MC1600 (Gelled isoparaffin from Penreco) | — | 99.92 | — |
| Versagel ME500 (Gelled hydrogenated polyisobutene from Penreco)) | — | — | 99.92 |
| Colorona Magenta Cosmetic Pigment (from Rona) | 0.08 | 0.08 | 0.08 |

The compositions described above can be prepared by conventional formulation and mixing techniques. Prepare the cleansing phase composition by first adding citric acid into water at 1:3 ratio to form a citric acid premix. Then, add the following ingredients into the main mixing vessel in the following sequence: water, Miracare SLB-365, sodium chloride, sodium benzoate, Disodium EDTA, glydant. Start agitation of the main mixing vessel. Then, add perfume into the batch. Keep agitation until a homogenous solution forms.

Prepare the benefit phase by adding Versagel into a mixing vessel. Heat the vessel to 190° F. Then, add cosmetic pigment with agitation. Let the vessel cool down with slow agitation.

The cleansing and benefit phases are density matched within 0.05 g/cm$^3$. Package both phases into a single container using conventional toothpaste-tube filler equipment. The sample stage spins the bottle during the filling process to create a striped appearance. The stripe size is about 6 mm in width and 100 mm in length.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal cleansing article comprising a package containing a striped personal cleansing composition comprising:
   (a) a first stripe comprising a cleansing phase comprising a surfactant, an electrolyte comprising an anion selected from the group consisting of phosphate, chloride, sulfate, citrate and mixtures thereof and a cation selected from the group consisting of sodium, ammonium, potassium, magnesium and mixtures thereof, a density modifier comprising a low density microsphere and water, wherein the electrolyte is present from about 0.1% to about 15% by weight of the first stripe; and
   (b) at least one additional stripe comprising a benefit phase that is substantially free of surfactant and substantially anhydrous and comprising at least about 20%, by weight of said benefit phase, of a hydrophobic skin benefit agent having a Vaughan Solubility Parameter of from about 5 to about 15 (cal/cm$^3$)$^{0.5}$; and
   wherein the first stripe and the at least one additional stripe have substantially the same density.

2. A personal cleansing article according to claim 1, wherein said low density microsphere comprises a particle having a density lower than 0.7 g/cm$^3$.

3. A personal cleansing article according to claim 1 wherein said low density microsphere is comprised of a material selected from the group consisting of inorganic material, organic material and mixtures thereof.

4. A personal cleansing article according to claim 1, wherein the benefit phase has a Consistency value of from about 1 poise to about 10,000 poise.

5. A personal cleansing article according to claim 1, wherein the benefit phase has a Shear Index of from about 0.1 to about 0.8.

6. A personal cleansing composition according to claim 1, wherein the hydrophobic material represents at least about 50% by weight of the benefit phase.

7. A personal cleansing article according to claim 1, wherein said hydrophobic skin benefit agent is selected from the group consisting of petrolatum, mineral oil, micro-crystalline waxes, paraffins, ozokerite, polyethylene, polybutene, polydecene, perhydrosqualene, dimethicones, cyclomethicones, alkyl siloxanes, polymethylsiloxanes, methylphenylpolysiloxanes, lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, castor oil, soy bean oil, sunflower seed oil, maleated soy bean oil, safflower oil, cotton seed oil, corn oil, walnut oil, peanut oil, olive oil, cod liver oil, almond oil, avocado oil, palm oil, sesame oil, and combinations thereof.

8. A personal cleansing article according to claim 1, wherein said personal cleansing composition further comprises a structurant.

9. A personal cleansing article according to claim 8, wherein the structurant is selected from the group consisting of trihydroxystearin, silicas, clays, and polymers.

10. A personal cleansing article according to claim 1, wherein said personal cleansing composition further comprises a cationic deposition polymer.

11. A personal cleansing article according to claim 1, wherein the first stripe and the at least one additional stripe form a pattern within the package.

12. A personal cleansing article composition according to claim 1, wherein said package is transparent.

* * * * *